US005500373A

United States Patent [19]
Lehrer

[11] Patent Number: 5,500,373
[45] Date of Patent: Mar. 19, 1996

[54] METHODS FOR DETERMINING THE CONCENTRATION OF CYANIDE IN SOUR AQUEOUS SYSTEMS

[75] Inventor: Scott E. Lehrer, Houston, Tex.

[73] Assignee: Betz Laboratories, Inc., Trevose, Pa.

[21] Appl. No.: 410,241

[22] Filed: Mar. 24, 1995

[51] Int. Cl.⁶ .................................................. G01N 31/00
[52] U.S. Cl. ............................................ 436/109; 436/119
[58] Field of Search ...................................... 436/109, 119, 436/6; 423/366

[56] References Cited

U.S. PATENT DOCUMENTS

| | | | |
|---|---|---|---|
| 4,804,631 | 2/1989 | Lue-Hing et al. | 436/109 |
| 5,431,877 | 7/1995 | Brücken et al. | 422/7 |

FOREIGN PATENT DOCUMENTS 0046191  9/1993  Japan .

OTHER PUBLICATIONS

Ingersoll et al., "Development and Evaluation of Procedures for the Analysis of Simple Cyanides, Total Cyanides, and Thiocyanate in Water and Wastewater", U.S. Dept. of Commerce, National Technical Information Service, Oct. 1983.

Kuban et al., "Selective Determination of Gases by Two–Stage Membrane Differentiated Flow Injection Analysis. Determination of Trace Hydrogen Cyanide in the Presence of Large Concentrations of Hydrogen Sulfide", Anal. Chem., 1992, 64, 1106–1112.

Luthy et al., "Determination of Cyanide Levels in Hygas Wastewater", Environmental Studies Institute–Carnegie Mellon University, Pittsburgh, PA, Nov. 1978.

Sweileh, "Determination of Cyanide and Thiocyanate By A Spectro–photometric Flow–Injection Method", Analytica Chimica Acta, 220 (1989), pp. 65–74.

Meeussen et al., "Spectrophotometric Determination of Total Cyanide, Iron–Cyanide Complexes, Free Cyanide and Thiocyanate In Water By A Continuous–Flow System", Analyst, vol. 114, Aug. 1989, pp. 959–963.

*Primary Examiner*—James C. Housel
*Assistant Examiner*—Rachel Heather Freed
*Attorney, Agent, or Firm*—Alexander D. Ricci; Philip H. Von Neida

[57] ABSTRACT

A method for determining the concentration of cyanide in an aqueous system is disclosed. The method determines the cyanide concentration from a determination of reference thiocyanate concentrations and will measure the cyanide concentration in the presence of sulfides.

9 Claims, No Drawings

05,500,373

METHODS FOR DETERMINING THE CONCENTRATION OF CYANIDE IN SOUR AQUEOUS SYSTEMS

FIELD OF THE INVENTION

The present invention relates to methods for determining the concentration of cyanide in aqueous systems. The present invention will effectively measure the amount of cyanide in an aqueous system where $H_2S$ and thiocyanate are present.

BACKGROUND OF THE INVENTION

Corrosion, particularly of ferrous metals, in crude oil producing, collection and refining systems is a significant problem. The adverse effects of corrosion which shorten equipment life and increase downtime have multiplied as the refinery process has expanded and become more complex. Corrosion problems in a refinery operation can be the result of any one or a combination of the components found in the crude oil, the chemicals used in the refinery process, and the process conditions.

In many hydrocarbon refining streams there is an aqueous phase present therein. The aqueous phase is simply water entrained in the hydrocarbons being processed and/or water added to the system for purposes such as stripping. Oftentimes contaminants are present in the aqueous phase and they contribute to the problems of corrosion in various refinery processes.

With sour crudes, an additional corrodent is $H_2S$, either originally present in the sour oil or gas and/or formed at processing temperatures by decomposition of sulfur compounds in the charge stocks. Other contaminants such as $NH_3$ and HCN are found in alkaline waters downstream of fluidized catalytic cracking units (FCCU), cokers and other hydroprocessing units, and in alkanolamine units.

The presence of cyanide can promote hydrocarbon damage of carbon steels exposed to aqueous sour steams. The inhibition of corrosion caused by cyanide and sulfur compounds is of great interest in the refining industry.

However, treatment programs are not readily determined due to industry problems with accurately measuring free cyanide in samples containing sulfide. Typically, the ratio of $H_2S$ to HCN is from 10:1 to 1000:1 in these systems. Sulfide must be removed from the sample at the time of collection to prevent the potential reaction of cyanide with sulfur oxidation products, i.e., polysulfide. If sulfide is left in the sample, it can be oxidized by entrained oxygen to polysulfide which can react with cyanide and lead to erroneous results. Sulfide also interferes with current cyanide measuring methods such as the Selective Ion Electrode and trying to remove the sulfide by, for example, precipitation as a metal sulfide salt, can also remove a significant amount of cyanide as an insoluble metal cyanide complex making a determination of cyanide concentration difficult.

The present inventor has discovered a method for determining the concentration of cyanide in an aqueous system where sulfide and thiocyanate are present. The present invention measures the conversion of cyanide to thiocyanate by fixation of samples through two separate procedures. This measured difference in thiocyanate levels allows for determining cyanide concentration without the concern of $H_2S$ levels and the inherent dangers in handling cyanide.

DESCRIPTION OF THE RELATED ART

Sulfide and thiocyanate are discussed as interferences in an analysis for total cyanides in Ingersoll et al., "Development and Evaluation of Procedures for the Analysis of Simple Cyanides, Total Cyanides, and Thiocyanate in Water and Wastewater," U.S. Dept. of Commerce—National Technical Information Service, p. 12, Oct. 1983. Seven possible methods for the analysis of simple cyanides in the presence of sulfide and thiocyanate were investigated. Of the methods studied, only the modified Roberts-Jackson gave accurate determination of simple cyanides in the presence of sulfide and thiocyanate. This method is based on converting to hydrocyanic acid all but the most stable metal-cyanide complexes from a slightly acidified sample. The modified Roberts-Jackson procedure differs from the present invention in that it requires distillation of the cyanide (as HCN) and absorption in a sodium hydroxide solution and that the cyanide is analyzed for directly. The present invention does not employ a distillation step and the cyanide is analyzed for indirectly based on its conversion to thiocyanate.

In Kuban et al., "Selective Determination of Gases by Two-Stage Membrane Differentiated Flow Injection Analysis. Determination of Trace Hydrogen Cyanide in the Presence of Large Concentrations of Hydrogen Sulfide", Anal. Chem., 1992, 64, 1106–1112, hydrogen cyanide concentration is determined in the presence of hydrogen sulfide. Hydrogen cyanide and hydrogen sulfide diffuse through a porous poly(vinylidene difluoride) (PVDF) tubular membrane into a NaOH absorber and are separated based on their relative diffusivities. The pH is adjusted to 9.5–10, and the liberated HCN is selectively permeated across a tubular silicone rubber membrane into a NaOH absorber. Kuban does not teach conversion to thiocyanate.

Luthy, et al., "Determination of Cyanide Levels in Hygas Wastewater", Environmental Studies Institute—Carnegie Mellon University, Pittsburgh, Penn., Nov. 1978, teaches the use of sulfide precipitation and filtration and alkaline pH adjustment in cyanide analysis in Hygas raw quench water. In both the present invention and Luthy, cyanide is determined in the presence of both sulfide and thiocyanate. However, Luthy differs from the present invention in that Luthy requires pH adjustment to >12 and cyanide is analyzed for directly.

Sweileh, "Determination of Cyanide and Thiocyanate by a Spectrophotometric Flow-Injection Method", Analytical Chimica Acta, 220 (1989), pp. 65–74, describes a spectrophotometric flow-injection method for the determination of cyanide and thiocyanate. The method involves a two-step procedure in which the total concentration of both species is determined using sodium-isonicotinate/sodium barbiturate reagents, after which the cyanide is complexed with nickel (11) and thiocyanate is quantified separately; and the cyanide concentration is calculated by difference.

Meeussen et al., "Spectrophotometric Determination of Total Cyanide, Iron-Cyanide Complexes, Free Cyanide and Thiocyanate in Water by a Continuous-Flow System", Analyst, Vol. 114, August 1989, pp. 959–963, describes a continuous flow technique combined with spectrophotometric detection. The distinction between iron-cyanide complexes and free cyanide plus thiocyanate was made by UV irradiation and distillation with citric acid. The distinction between free cyanide and thiocyanate was made by masking the free cyanide with formaldehyde.

DETAILED DESCRIPTION OF THE INVENTION

The present invention relates to a method for determining the concentration of cyanide in an aqueous system where thiocyanate and sulfide are both present comprising:

a) determining the background thiocyanate concentration (SCN background) in a background sample by
  i) adding to said background sample a sufficient amount of a metal salt to precipitate sulfide but not strongly complex thiocyanate;
  ii) preferably, removing the precipitated metal sulfide from the background sample solution;
  iii) measuring the thiocyanate concentration in the background sample;
b) determining the final thiocyanate concentration (SCN final) in a final sample by
  i) adding to said final sample a sufficient amount of a polysulfide compound to convert cyanide to thiocyanate and allowing for a reaction period sufficient for the polysulfide to convert cyanide to thiocyanate;
  ii) adding a sufficient amount of a metal salt to precipitate sulfide from the final sample but not to strongly complex thiocyanate, and preferably removing the metal sulfide from solution;
  iii) measuring the thiocyanate concentration in the final sample; and
c) calculating the cyanide concentration in the aqueous system from the thiocyanate concentrations determined in steps (a(iii)) and (b(iii)) using the formula:
Concentration of cyanide=(SCN Final–SCN Background)×0.448

The metal salt employed can be any metal salt which will form an insoluble sulfide salt while not strongly complexing thiocyanate. By not strongly complexing, it is meant that the logarithm of the first formation constant (defined in Lange's Handbook of Chemistry, 13th Ed. 1985) is less than or equal to 2. Due to their relatively low toxicities, the preferred metal salts are those of zinc such as zinc acetate but the inventor anticipates that lead salts and cadmium salts will also be effective in the methods of the present invention.

The metal salt should be added to the background sample in an amount which is sufficient to precipitate the hydrogen sulfide in the sample. This reaction between the metal salt and the hydrogen sulfide will "fix" the sulfide and inhibit the oxidative conversion of sulfide to polysulfide and thus inhibit conversion of residual cyanide to thiocyanate. Removal of the precipitate, metal sulfide, from solution will eliminate any further conversion of cyanide to thiocyanate. For purposes of this invention, fix or fixation is the term used to describe the method of preventing the conversion of cyanide to thiocyanate. The amount of metal salt added to the first reference sample will be dependent upon the amount of hydrogen sulfide present in the sample. Using zinc acetate for example, it should be added in an amount which will result in at least a 1:1 equivalence ratio of zinc: sulfide.

The polysulfide compound can be any inorganic or organic polysulfide compound which will convert the cyanide present in the final reference sample to thiocyanate. Preferably, the polysulfide is selected from the group consisting of ammonium polysulfide and sodium polysulfide. The present inventor anticipates that the addition of a material which will cause the in situ generation of a polysulfide compound in the final reference sample will be effective in the methods of the present invention.

The polysulfide compound should be added to the final sample in an amount sufficient to convert all the cyanide to thiocyanate. For example, the addition of 1,000 ppmv of ammonium polysulfide (containing 45 wt % elemental sulfur) was found to convert all the cyanide to thiocyanate when added to particular samples. The amount of polysulfide added will of course be dependent on the amount of cyanide present in the final sample.

For example, using typically available commercial sources of ammonium polysulfide which contain 40–45% by weight, a weight ratio of ammonium polysulfide solution to cyanide should be at least 2.5:1. In general, 1,000 ppm of commercial ammonium polysulfide solutions containing 40–45 wt % sulfur should be sufficient to convert all the cyanide contained in aqueous sour streams found in various refinery processing units.

The concentration of thiocyanate in the samples may be measured by standard analytical techniques such as spectrophotometry, titrimetry, colorimetry and potentiometry. The use of these methods is dependent upon the interferences present in the sample and the ability to eliminate said interferences from a given sample of water.

The final concentration of cyanide may be calculated using the following equation:
Concentration of cyanide in ppm=(final thiocyanate-background thiocyanate)
×MW of cyanide (26)/MW of thiocyanate (58)

The methods of the present invention are particularly effective in hydrocarbon processing systems which contain an aqueous phase therein. Such systems include but are not limited to alkanolamine units, FCC units and coking units.

In order to more clearly illustrate this invention, the data set forth below were developed. The following examples are included as illustrations of the invention and should not be construed as limiting the scope thereof.

EXAMPLES

The concentration of free cyanide ($CN^-$) in sour waters from various refineries was determined using the inventive method. ① One bottle (background sample) was filled with 20 mL of a 22.5% zinc acetate solution. A second bottle (final sample) was prepared with 1 mL of a 10% ammonium polysulfide solution in $NH_4OH$.

② 100 ml of the sour water sample was added to each (background and final sample) bottle. ③ Lead acetate paper was used to verify that the sample in the background sample bottle was sweet (no immediate brown color change in the paper).

④ 50 to 100 ml of the background sample were placed into a centrifuge tube and centrifuged to obtain a clear aqueous layer. ⑤ After centrifuging, 20 mL of the sample was pulled into a syringe and 10 mL was discharged through a filter into a clean graduated cylinder. Deionized water was added to dilute the background sample to between 0.1 and 200 ppm $SCN^-$. Thiocyanate concentrations were determined by a variation of Test Method 4500⁻ $CN^-$ N. Thiocyanate from Standard Methods for the Examination of Water and Wastewater, 18th Edition. ⑥ 10 mL of the diluted sample was added to a clean beaker and adjusted to pH of 2 with concentrated $HNO_3$. 0.5 mL of ferric nitrate solution was added and this solution was mixed.

⑦ Within 5 minutes of adding the ferric nitrate solution, the absorbance at 460 nm was measured using a calibrated (to $SCN^-$) spectrophotometer. The absorbance was compared against a standard $SCN^-$ curve. Based on the standard curve and measured absorbance, the ppm measured was determined. ⑧ The thiocyanate concentration ($SCN_{background}$) was then calculated by the equation:

$$SCN_{background} = A \times \text{dilution factor}_{background} \times \left( \frac{C+E}{C} \right)$$

To determine $SCN^-$ in the final sample, this sample was treated with zinc acetate until sweet as determined with lead acetate paper and the total volume of the sample was determined. Steps 4 through 8 were repeated, substituting the final sample for the background sample. The thiocyanate concentration ($SCN_{final}$) was then calculated by the equation:

$$SCN_{final} = \frac{(A \times B) \times (C + D + E)}{C}$$

A=ppm measured
B=dilution factor$_{final}$
C=mL of sample
D=mL of 1% ammonium polysulfide
E=mL of zinc acetate solution The determination of free cyanide was made using the calculation:

Concentration of cyanide=($SCN_{final}$–$SCN_{background}$)× 0.448

The results of this testing are reported in Table I.

TABLE I

| | Cyanide spike recoveries in refinery sour waters | | | | |
|---|---|---|---|---|---|
| Sour Water Stream | Background SCN⁻ | Final SCN⁻ | ppm CN⁻ | ppm CN⁻ Spike | % spike recovered |
| FCCU gas from a | 4.3 | 74 | 31 | — | — |
| Southern refinery (I) | 4.3 | 94 | 40 | 10 | 90 |
| | 4.3 | 170 | 74 | 47 | 94 |
| FCCU gas from a | 2.4 | 40 | 17 | — | — |
| Southern refinery (II) | 2.4 | 138 | 61 | 47 | 94 |
| FCCU gas from a | 3.7 | 78 | 33 | — | — |
| Southern refinery (III) | 3.7 | 138 | 60 | 29 | 93 |
| | 3.8 | 170 | 75 | 48 | 88 |
| Alkanolamine scrubbing unit | 0.7 | 1.4 | 0.3 | — | — |
| unit from a Western refinery | 0.7 | 24 | 10.5 | 9.9 | 103 |
| | 0.7 | 106 | 47 | 47 | 100 |
| Unsaturated gas plant | 8.7 | 114 | 47 | — | — |
| from a Southern refinery | 8.7 | 143 | 60 | 19 | 68 |
| | 8.7 | 269 | 117 | 94 | 74 |

FCCU gas samples I, II and III were collected at different dates.

As seen in Table I, most spike recoveries were within 10% of the expected value. The samples that tested outside 10% were probably the result of inaccuracies in preparing or delivering the cyanide standard or interference due to complexation of added cyanide by soluble iron.

These results indicate that accurate determinations of cyanide concentrations in sour water streams can be made by determining thiocyanate concentrations.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for determining the concentration of cyanide in an aqueous system where thiocyanate and sulfide are present comprising:
   a) determining the background thiocyanate concentration (SCN background) in a background sample by
      i) adding to said background sample a sufficient amount of a metal salt to precipitate sulfide but not strongly complex thiocyanate;
      ii) removing the precipitated metal sulfide from the background sample;
      iii) measuring the thiocyanate concentration in said background sample;
   b) determining the final thiocyanate concentration (SCN final) in a final sample by
      i) adding to said final sample a sufficient amount of a polysulfide compound to convert the cyanide present to thiocyanate and allowing for sufficient time for said polysulfide to convert said cyanide;
      ii) adding to said final sample a sufficient amount of a metal salt to precipitate sulfide but not strongly complex thiocyanate;
      iii) measuring the thiocyanate concentration in said final sample;
   c) calculating the cyanide concentration in said aqueous system using the formula:
      Concentration of cyanide=(SCN final–SCN background)×0.448

2. The method as claimed in claim 1 wherein said metal salt is a zinc salt.

3. The method as claimed in claim 2 wherein said zinc salt is zinc acetate.

4. The method as claimed in claim 1 wherein said polysulfide compound is selected from the group consisting of ammonium polysulfide and sodium polysulfide.

5. The method as claimed in claim 1 wherein said polysulfide compound is generated in situ in said aqueous system.

6. The method as claimed in claim 1 wherein said thiocyanate concentration is determined by spectrophotometry.

7. The method as claimed in claim 1 wherein said salt is added to said background sample in at least a 1:1 equivalence ratio with said sulfide in said sample.

8. The method as claimed in claim 4 wherein said ammonium polysulfide compound contains 45 weight % sulfur.

9. The method as claimed in claim 8 wherein said ammonium polysulfide compound is added to said final sample in at least a 2.5:1 weight/weight ratio to said cyanide in said sample.

* * * * *